US 6,650,730 B2

(12) United States Patent
Bogatu et al.

(10) Patent No.: US 6,650,730 B2
(45) Date of Patent: *Nov. 18, 2003

(54) FILTER ASSEMBLY FOR X-RAY FILTER SYSTEM FOR MEDICAL IMAGING CONTRAST ENHANCEMENT

(75) Inventors: Ioan Niculae Bogatu, San Diego, CA (US); Jin-Soo Kim, San Diego, CA (US)

(73) Assignee: Fartech, Inc., San Diego, CA (US)

( * ) Notice: Subject to any disclaimer, the term of this patent is extended or adjusted under 35 U.S.C. 154(b) by 52 days.

This patent is subject to a terminal disclaimer.

(21) Appl. No.: 10/062,010

(22) Filed: Jan. 31, 2002

(65) Prior Publication Data

US 2002/0191751 A1 Dec. 19, 2002

Related U.S. Application Data

(63) Continuation-in-part of application No. 09/767,992, filed on Jan. 23, 2001.

(51) Int. Cl.$^7$ ................................................ G21K 3/00
(52) U.S. Cl. ...................... 378/158; 378/62; 378/156; 378/157
(58) Field of Search .............................. 378/51, 62, 66, 378/157, 158, 159, 160, 161, 156

(56) References Cited

U.S. PATENT DOCUMENTS

| 4,254,778 A | 3/1981 | Clow |
| 4,296,378 A | 10/1981 | King |
| 4,498,048 A | 2/1985 | Lee |
| 4,656,425 A | 4/1987 | Bendel |
| 4,766,378 A | 8/1988 | Danby |
| 4,829,252 A | 5/1989 | Kaufman |
| 4,870,363 A | 9/1989 | Yassine |
| 4,887,604 A | * 12/1989 | Shefer et al. ............... 600/431 |
| 5,099,208 A | 3/1992 | Fitzpatrick |
| 5,184,074 A | 2/1993 | Arakawa et al. |
| 5,755,666 A | 5/1998 | Bornert |
| 6,061,426 A | 5/2000 | Linders |
| 6,094,468 A | 7/2000 | Wilting |

OTHER PUBLICATIONS

Zeman et al., Contrast Agent Choice for Intravenous Coronary Angiography, 1990, Nuclear Instruments and Methods in Physics Research A291, 67–93, North–Holland.

Dilmanian et al., CT with Monochromatic Synchrotron X Rays and Its Potential in Clinical Research, 1997, SPIE vol. 3149.

* cited by examiner

Primary Examiner—David V. Bruce
Assistant Examiner—Courtney Thomas

(57) ABSTRACT

A system for creating an image of the internal features of an object includes an X-ray source and detector array positioned to interpose the object between the X-ray source and the detector array. An X-ray beam is passed through the object along a first path. While passing through the object, the beam is successively filtered twice, each time with a different filter. The successive filtration of the beam results in the production of two electrical signals by the detector which are processed to create an image signal for the path. The process is repeated for a plurality of paths through the object and the resulting image signals are combined using traditional computer tomography techniques to produce a composite image of the object.

35 Claims, 6 Drawing Sheets

FILTER ASSEMBLY FOR X-RAY FILTER SYSTEM FOR MEDICAL IMAGING CONTRAST ENHANCEMENT

This application is a continuation-in-part of application Ser. No. 09/767,992, filed Jan. 23, 2001, which is currently pending. The contents of application Ser. No. 09/767,992 are incorporated herein by reference.

FIELD OF THE INVENTION

The present invention pertains generally to devices and methods for imaging the internal features of an object. More particularly, the present invention pertains to improved devices and methods for imaging the internal features of an object while using a conventional broadband X-ray source. The present invention is particularly, but not exclusively, useful for producing an enhanced-contrast image of the internal features of an object by using filtered X-ray radiation.

BACKGROUND OF THE INVENTION

The ability to image the internal features of an object is important in many applications. Two examples include medical diagnosis and the non-destructive testing of structural components to detect configuration or discover internal flaws. In all applications, it is desirable to produce an image having high contrast and spatial resolution. Radiation within the X-ray spectrum is often used to image internal features because of the ability of X-ray radiation to penetrate matter and because different matter absorbs X-ray radiation at different rates. Typically, a conventional X-ray source produces an emission of X-ray radiation having a broad range of energies. In conventional imaging applications, these X-rays are directed through the object for subsequent capture by a film or detector. The imaging films and detectors used are responsive to the intensity of the radiation received, and thus are able to produce an image of the internal features of the object when those internal features have differing absorption characteristics.

To enhance the contrast and spatial resolution of an image, contrast agents are often used. Specifically, these agents include chemical elements that have absorption rates that are significantly different than the constituents of the object to be imaged. For example, Iodine can be administered within the body as a contrast agent. Once administered, the Iodine is selectively absorbed by certain tissues or is present within the blood vessels. Subsequently, when an X-ray image is formed, areas of the body with large amounts of Iodine will absorb relatively greater amounts of X-ray radiation than areas of the body without Iodine. Thus, contrast agents can be used with good efficacy to increase both the contrast and the spatial resolution of the image.

FIG. 1 shows the variation of absorption coefficient with radiation energy for a typical chemical element. In simple terms, the absorption coefficient decreases as the energy increases until an energy is reached that is sufficient to knock a K-shell electron from it's orbit. At this energy, $E_{K-EDGE}$, the value of the absorption coefficient jumps. For purposes of the present disclosure, the term $K_{EDGE}$ is used to denote the energy at which the jump in absorption coefficient occurs. Continuing with FIG. 1, it can be seen that further increases in energy again result in a gradual decrease in absorption coefficient.

The present invention recognizes that the variation in absorption coefficient near $K_{EDGE}$ can be utilized to increase image contrast. Specifically, the present invention recognizes that image contrast can be increased by first introducing a contrast agent having a known $K_{EDGE}$ into the object. Next, a first image can be formed using radiation filtered by a first element having a $K_{EDGE}$ just less than $K_{EDGE}$ for the contrast agent and a second image formed using radiation filtered by a second element having a $K_{EDGE}$ just greater than $K_{EDGE}$ for the contrast agent. When this is done, the resulting two images can be subtracted to produce a high contrast image of the internal features of the object. This image is equivalent to the image obtained by using a quasi-monochromatic radiation having an energy band between $K_{EDGE,\ FIRST\ ELEMENT}$ and $K_{EDGE,\ SECOND\ ELEMENT}$.

A different way to produce the quasi-monochromatic X-ray radiation described above is to use a crystal monochromator. Unfortunately, when a crystal monochromator is used in conjunction with a conventional X-ray source, the intensity of the resulting monochromatic radiation is so reduced that the radiation is insufficient for almost all practical imaging uses. One way to produce monochromatic radiation at a suitable intensity for imaging is to pass the high intensity radiation from a synchrotron source through a double crystal monochromator. As can be expected, producing radiation with a synchrotron source is very expensive. Further, the beam produced by the synchrotron source/double crystal monochromator is fixed in direction and, consequently, cannot be rapidly moved as required in a typical tomographic scan.

In light of the above, it is an object of the present invention to provide devices and methods suitable for the purposes of producing a digital image signal that is substantially equivalent to an image signal obtained by passing quasi-monochromatic radiation (i.e. radiation having a narrow energy band) through an object. It is another object of the present invention to provide devices and methods for producing images of the internal features of an object having enhanced contrast and high spatial resolution. It is yet another object of the present invention to provide devices and methods for use in conjunction with standard computer tomography or angiography equipment to enhance the contrast and increase the spatial resolution of the images produced. It is yet another object of the present invention to provide devices and methods for enhancing image contrast and increasing spatial resolution that can be used with a variety of different contrast agents. Yet another object of the present invention is to provide an X-ray Filter System For Medical Imaging Contrast Enhancement which is easy to use, relatively simple to manufacture, and comparatively cost effective.

SUMMARY OF THE PREFERRED EMBODIMENTS

The present invention is directed to a system for creating an image of the internal features of an object. Specifically, the present invention is directed at imaging an object that contains a contrast agent. For the present invention, the system includes an X-ray source configured to produce a spectrum of X-ray radiation. An optional collimator may be provided to collimate the radiation emitted from the X-ray source into one or more beams. As such, each beam emanates from the X-ray source in a slightly different direction, and consequently, along a separate path. For the present invention, the X-ray source is oriented relative to the object to direct all such paths towards the object. Further, a mechanism is provided to move the X-ray source relative to the object to cause each radiation beam emanating from the X-ray source to successively travel on different paths through the object. For example, the X-ray source can be slideably mounted on a circular track that extends around the object.

A detector array is positioned on the opposite side of the object to interpose the object between the X-ray source and the detector array. Preferably, the detector array includes a plurality of detectors, one detector for each beam that emanates from the X-ray source/collimator assembly. Further, a mechanism can be provided to move the detector array as the X-ray source is moved. Specifically, the detector array can be moved to allow each detector to track a single X-ray beam, as that X-ray beam travels on successive paths through the object. In response to the receipt of an X-ray beam, the detector produces an electrical signal that is proportional to the intensity of the radiation received.

An important aspect of the present invention is that the X-ray radiation is filtered between the X-ray source and the detectors. Specifically, for each X-ray beam on each path, the beam is successively filtered twice, each time with a different filter. Each time the beam is moved to a new path, the beam is once again filtered two times. Each time the beam is successively filtered two times, two different electrical signals are produced by a detector. For the present invention, these two electrical signals can be manipulated by a processor to produce an image signal for the path. Once an image signal is established for each desired path, conventional tomography techniques can be used to combine all the image signals (one image signal for each path) into a composite image that reveals the internal features of the object.

For the present invention, a filter pair having two different filters is used to successively filter each beam on each path. In accordance with the present invention, a unique filter pair is designed for use with the specific contrast agent that is prescribed for introduction into the object. Specifically, the chemical constituents and thickness of each filter in the filter pair are determined with reference to the specific contrast agent that is being used. For a contrast agent with a chemical element having a $K_{EDGE,\ CONTRAST\ AGENT}$, a filter pair is used having a first filter with a chemical element having a $K_{EDGE}$ that is slightly greater than $K_{EDGE,\ CONTRAST\ AGENT}$, and, a second filter with a chemical element having a $K_{EDGE}$ that is slightly less than $K_{EDGE,\ CONTRAST\ AGENT}$.

A mechanism is provided to successively interpose each filter of the filter pair between the X-ray source and the object to thereby allow the successive filtration of the beams emanating from the X-ray source. For example, the filter pair can be mounted on an oscillating frame or a rotating wheel. For the embodiment with the wheel, the filter pair is mounted on the wheel, and a motor is provided to rotate the wheel about the wheel's axis. The wheel and motor can be attached to the X-ray source to allow the wheel, filters and motor to travel with the X-ray source/collimator assembly as the assembly moves with respect to the object.

In operation, first the contrast agent is introduced into the object, and the object is placed between the X-ray source and the detector array. Next, the X-ray source is located at a first position and activated to produce one or more beams travelling through the object on a first set of paths (one path for each beam). Next, the wheel containing the filters is rotated to successively interpose each filter of the filter pair between the X-ray source/collimator assembly and the object to filter each of the beams with each of the two filters. The result is the production of two intensity-proportional signals by the detector(s) for each path through the object.

For the present invention, these two signals can be manipulated either on-line or off-line by a processor to produce an image signal for the corresponding path. Specifically, the processor subtracts the digital signal produced by the detector with the second filter interposed along the path from the digital signal produced by the detector with the first filter interposed along the path. The result of this is an image signal that simulates the image signal that would be obtained if a quasi-monochromatic beam having an average energy approximately equal to the energy of $K_{EDGE,\ CONTRAST\ AGENT}$ were to be passed through the object along the path.

Once image signals are obtained for the first set of paths, the X-ray source/collimator assembly can be moved to a second position to cause the beams emanating from the assembly to travel along a new set of paths. While the X-ray source/collimator assembly is at the second position, the wheel is again rotated to successively interpose both filters between the X-ray source/collimator assembly and the object to again filter each of the beams with each of the filters. Again, two intensity-proportional signals are produced by a detector for each beam. For the present invention, these two signals can be manipulated by a processor as described above to produce an image signal for each new path. This process of moving the X-ray source/collimator assembly and producing an image signal for each new path can be repeated as desired. Further, it is to be appreciated that the X-ray source/collimator assembly can be moved at a continuous rate around the object. When this technique is used, the wheel containing the filters can be rotated continuously as the X-ray source moves. By rotating the wheel very rapidly, each beam is effectively filtered by each of the two filters before significant movement of the beam occurs. Thus, in effect, each beam remains on a single path while the successive filtration takes place. Once image signals are produced for all paths of interest, conventional tomography techniques can be used to combine all the image signals (one image signal for each path) into a composite image that shows the internal features of the object.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 2:
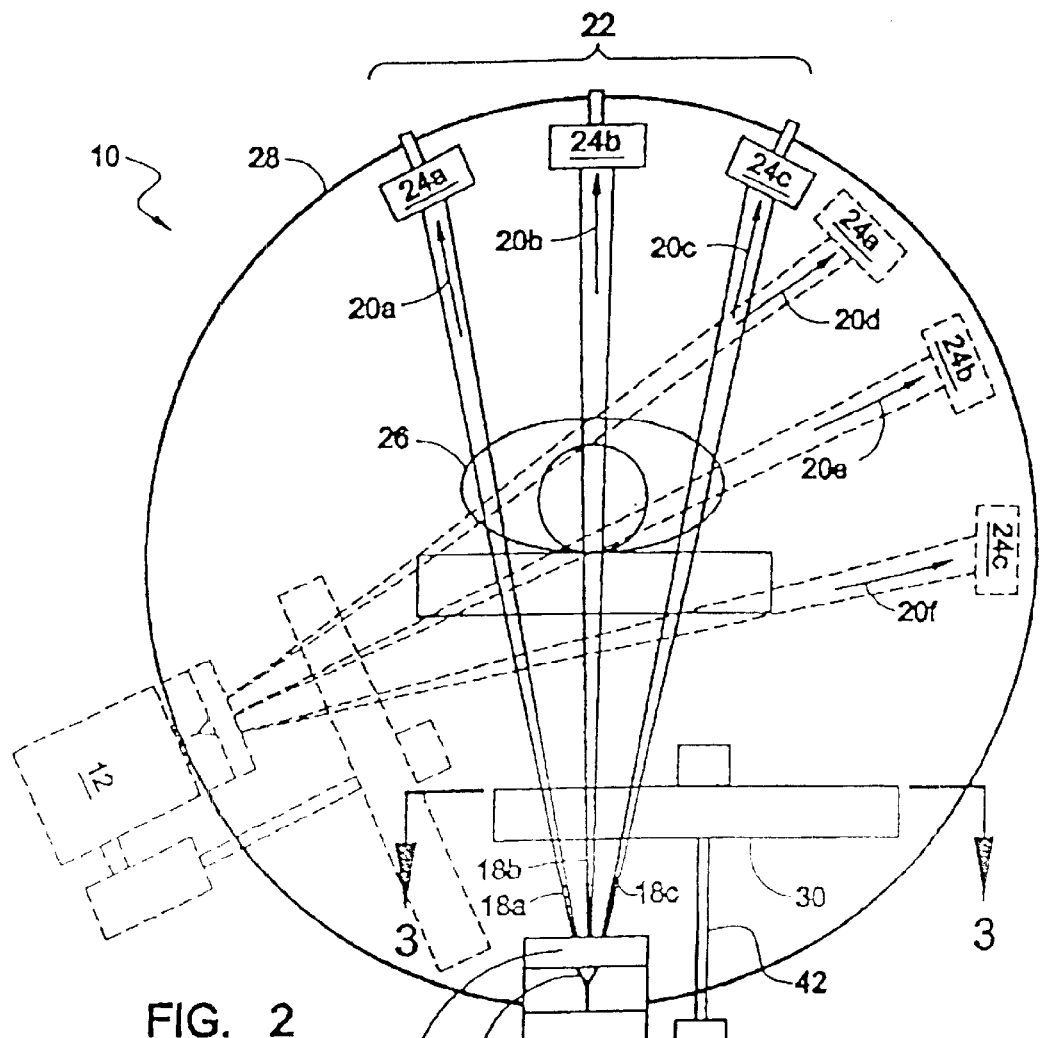
FIG. 2 is a plan view of a system in accordance with the present invention shown imaging a portion of a human body.

Referring initially to FIG. 2, an imaging system in accordance with the present invention is shown and generally designated 10. As shown in FIG. 2, the system 10 includes an X-ray source 12 configured to produce a spectrum of X-ray radiation 14. An optional collimator 16 may be provided to collimate the radiation 14 emitted from the X-ray source 12 into one or more beams 18a–c. As such, each beam 18 emanates from the X-ray source 12 in a slightly different direction, and consequently, along a separate path 20a–c. It is to be appreciated that the use of three beams 18 is merely exemplary and that as many beams 18 as desired may be used in accordance with the present invention. In detail, as shown in FIG. 2, beam 18a initially travels substantially along path 20a, beam 18b initially travels substantially along path 20b and beam 18c initially travels substantially along path 20c.

Referring still to FIG. 2, a detector array 22 is shown positioned to receive the beams 18 from the source 12. Specifically, the detector array 22 is shown having three detectors 24a–c, with detector 24a positioned to receive beam 18a, detector 24b positioned to receive beam 18b and detector 24c positioned to receive beam 18c. For the present invention, an object 26 can be interposed between the X-ray source 12 and the detector array 22 to thereby allow the beams 18 to be modified by passing through the object 26 before reaching the detectors 24. In accordance with the present invention, the detectors 24 can be any type of detector known in the pertinent art capable of receiving radiation and producing an electrical signal that is proportional to the intensity of the radiation received. For example, the detectors 24 can be solid state detectors (separate or having a charge couple detector structure), gas-filled detectors or scintillators with photo-multipliers. Preferably, each detector 24 is a small-area X-ray detector. For the present invention, the output of each detector 24 is electrically wired to a computer (not shown) to allow the signals generated by the detectors 24 to be processed.

Also shown in FIG. 2, the X-ray source 12 can be slideably mounted on a circular track 28 that extends around the object 26. Additionally, as shown, each detector 24 or the entire detector array 22 can be slideably mounted on the track 28. As such, the X-ray source 12 and detectors 24 can be moved either continuously or incrementally around the track 28 and relative to the object 26. The dashed lines in FIG. 2 show an exemplary second position for the X-ray source 12 and detectors 24. By moving the X-ray source 12, each radiation beam 18 emanating from the X-ray source 12 can be caused to successively travel on different paths 20 through the object 26. For example, as shown in FIG. 2, when X-ray source 12 is in the initial position represented by the solid lines, beam 18a travels substantially along path 20a, and when X-ray source 12 is moved to a second position represented by dashed lines, beam 18a travels substantially along path 20d. Similarly, beam 18b travels substantially along path 20e and beam 18c travels substantially along path 20f when the X-ray source 12 is in the position indicated by dashed lines. Accordingly, the detector array 22 can be moved in conjunction with the X-ray source 12 to allow each detector 24 to track a single X-ray beam 18, as that X-ray beam 18 travels on successive paths 20 through the object 26.

An important aspect of the present invention is that the X-ray radiation 14 is filtered between the X-ray source 12 and the detectors 24. By cross-referencing FIGS. 2 and 3, it can be seen that a wheel 30 having two attached filters 32, 34 can be used to successively filter each X-ray beam 18a–c on each path 20. As further shown, a motor 40 having a shaft 42 can be used to rotate the wheel 30 and filters 32, 34 to successively filter each beam 18 twice while the beam 18 travels substantially along a single path 20. Thus, for a path 20, the beam 18 is first filtered with filter 32 and then filtered with filter 34. Additionally, each time a beam 18 is moved to a new path 20, the wheel 30 is rotated through one complete revolution to once again successively filter the beam 18 with each filter 32, 34. Alternatively, the wheel 30 can be located between the X-ray source 12 and the collimator 16 (this configuration not shown). As shown, a bracket 44 can be used to attach the motor 40 to the X-ray source 12 to allow the wheel 30, the filters 32, 34, the motor 40 and the shaft 42 to travel with the X-ray source 12 as the source 12 moves along the track 28 relative to the object 26. Each time a beam 18 is successively filtered by filter 32 and filter 34, two different electrical signals are produced by a detector 24 (i.e. one electrical signal for filtration with filter 32 and one electrical signal for filtration with filter 34). For the present invention, a computer processor (not shown) can be configured to manipulate the two electrical signals created for each path 20 to produce an image signal for the path 20. For example, each path 20 can be used to produce an image signal that represents a single pixel in the final image. Or stated another way, a computer processor can be configured to subtract, pixel by pixel, the digital images created by each filter 32, 34 to produce the contrast enhancement image. Once an image signal is established for each desired path 20, conventional tomography techniques known in the pertinent art can be used to combine all the image signals (one image signal for each path 20) into a composite image that shows the internal features of the object 26.

Figure 1:
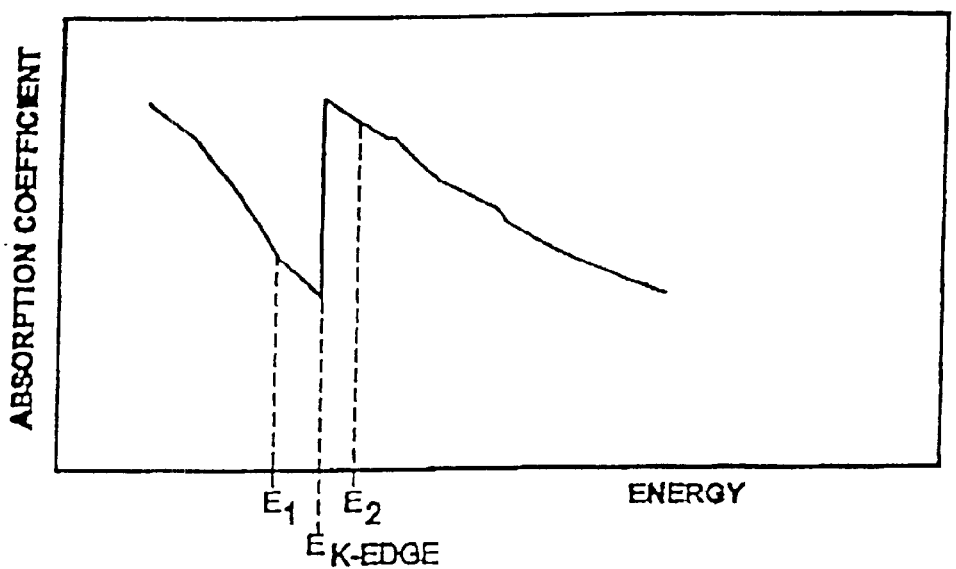
FIG. 1 is a graph showing the variation of absorption coefficient with radiation energy for a typical chemical element.
Figure 3:
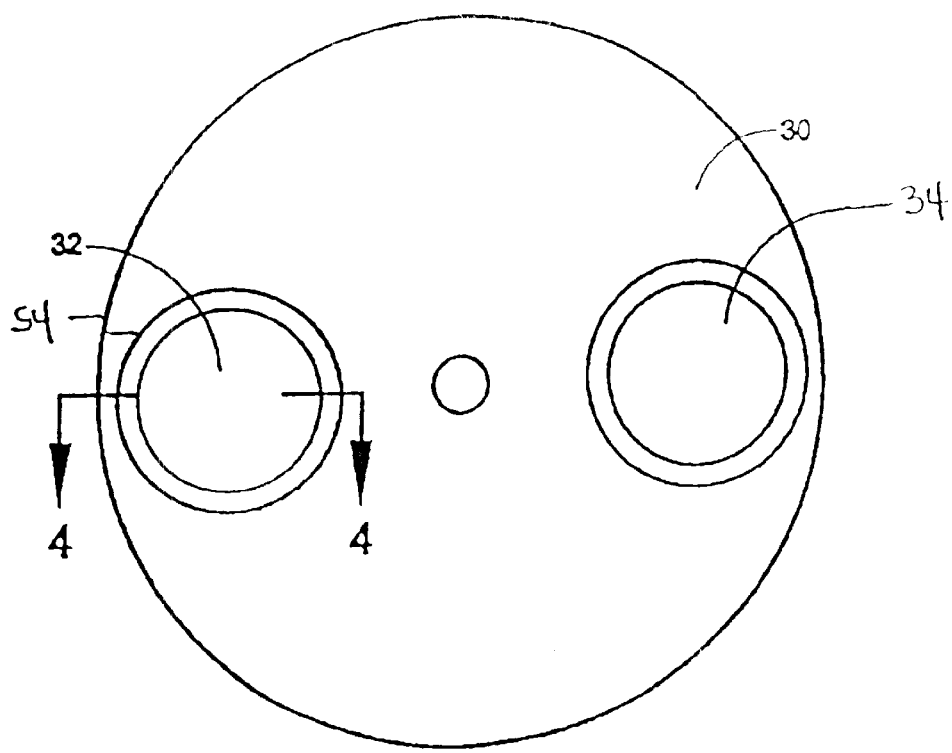
FIG. 3 is an elevational view of a filter pair and wheel as seen along line 3—3 in FIG. 2.
Figure 4:
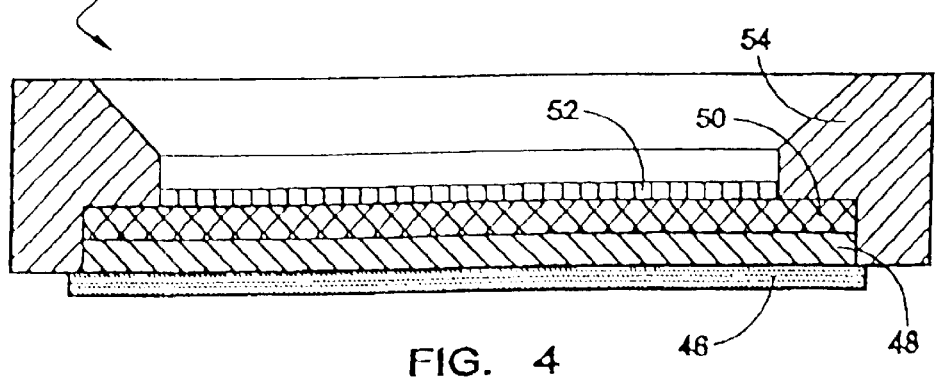
FIG. 4 is a cross-sectional view of a filter and filter holder as seen along line 4—4 in FIG. 3.

Referring now to FIG. 3, a filter pair having two different filters 32, 34 is mounted on the wheel 30 to allow each beam 18 on each path 20 to be successively filtered twice It is to be appreciated that a plurality of identical filter pairs, with each pair having two different filters 32, 34, can be mounted on the wheel 30 (multiple filter pair not shown). For example, when two identical filter pairs are used, the wheel 30 is rotated through 180 degrees for each path 18. As further detailed below, a unique filter pair is designed for use with a specific contrast agent that is prescribed for introduction into the object 26. Specifically, the chemical constituents and thickness of each filter 32, 34 is determined with reference to the specific contrast agent that is being used. FIG. 4 shows an exemplary filter 32 having layers 46, 48, 50 and 52. Specifically, the filter 32 can include an optional transparent layer 46, a filtering layer 48, an optional additional balance layer 50 and an optional protective layer 52. It is to be appreciated that each filter 32, 34 will have different layers 46, 48, 50, 52, the layers 46, 48, 50, 52 differing in both chemical makeup and thickness. For the present invention, the optional transparent layer 46 can be included to support as well as protect the other layers 48, 50, 52. The optional protective layer 52 can be included to protect the other layers 48, 50 from corrosion or other environmental factors. The function of the filtering layer 48 and the additional balance layer 50 are discussed below. As seen by cross-referencing FIGS. 3 and 4, a metal ring 54 can be used to hold the layers 46, 48, 50, 52 together and attach them to the wheel 30.

When used in conjunction with a contrast agent containing a chemical element having a $K_{EDGE,\ CONTRAST\ AGENT}$, a filter pair is constructed in accordance with the present invention having a filter 32 with a filtering layer 48 that contains a chemical element having a $K_{EDGE}$ that is greater than $K_{EDGE,\ CONTRAST\ AGENT}$, and a filter 34 with a filtering layer 48 that contains a chemical element having a $K_{EDGE}$ that is less than $K_{EDGE\ CONTRAST\ AGENT}$. The invention includes specific chemical elements and thickness' sufficient to create filter pairs for various contrast agents as shown in Table 1.

Referring back to FIG. 2, in the operation of the present invention, a contrast agent is first introduced into the object 26. Once introduced, the contrast agent will be selectively absorbed or localized in specific regions to thereby establish portions of the object 26 having differing concentrations of contrast agent. Table 1, below, lists a number of suitable contrast agents that are either in current use for imaging portions of the human body or are contemplated for future use. It is to be appreciated that conventional methods of administering the contrast agent that are known in the pertinent art can be employed. Further, it is anticipated that the present invention is applicable to the imaging of a non-human object 26, such as a structural component for a machine or device (not shown). In this case, a material in the structural component can be used as a contrast agent and a suitable filter pair constructed accordingly.

TABLE 1

Combinations of useable contrast elements and filter elements to be applied to $K_{EDGE}$ subtraction technique for image contrast enhancement

| Contrast Element | Atomic Number Z | $K_{EDGE}$, (CONTRAST AGENT) keV | Filter 32 chemical element and thickness ($\mu$m) | Filter 34 chemical element and thickness ($\mu$m) |
| --- | --- | --- | --- | --- |
| I  | 53 | 33.17 | $^{55}$Cs 290.0 | $^{52}$Te 102.0 |
| Xe | 54 | 34.56 | $^{56}$Ba 180.0 | $^{52}$Te 123.0 |
| Cs | 55 | 35.98 | $^{56}$Ba 180.0 | $^{53}$I 148.0 |
| Ba | 56 | 37.44 | $^{57}$La 105.0 | $^{55}$Cs 380.0 |
| Sm | 62 | 46.83 | $^{63}$Eu 136.0 | $^{60}$Nd 117.0 |
| Eu | 63 | 48.52 | $^{64}$Gd 120.0 | $^{62}$Sm 138.0 |
| Gd | 64 | 50.24 | $^{65}$Tb 140.0 | $^{63}$Eu 236.0 |
| Tb | 65 | 51.99 | $^{66}$Dy 130.0 | $^{64}$Gd 151.0 |
| Dy | 66 | 53.79 | $^{67}$Ho 130.0 | $^{65}$Tb 149.0 |
| Ho | 67 | 55.62 | $^{68}$Er 130.0 | $^{66}$Dy 149.0 |
| Er | 68 | 57.48 | $^{69}$Tm 135.0 | $^{67}$Ho 156.0 |
| Lu | 71 | 63.31 | $^{72}$Hf 110.0 | $^{70}$Yb 235.0 |
| Hf | 72 | 65.35 | $^{73}$Ta 97.0 | $^{71}$Lu 175.0 |
| Ta | 73 | 67.42 | $^{74}$W 84.0 | $^{72}$Hf 131.0 |
| W  | 74 | 69.52 | $^{75}$Re 80.0 | $^{73}$Ta 108.0 |
| Re | 75 | 71.68 | $^{76}$Os 80.0 | $^{74}$W 100.0 |
| Os | 76 | 73.87 | $^{77}$Ir 80.0 | $^{75}$Re 90.0 |
| Ir | 77 | 76.11 | $^{78}$Pt 90.0 | $^{76}$Os 92.0 |
| Bi | 83 | 90.53 | $^{90}$Th 170.0 | $^{82}$Pb 230.0 |

Once a contrast agent has been introduced, the object 26 can be placed between the X-ray source 12 and the detector array 22 as shown in FIG. 2. Next, the X-ray source 12 is located at a first position and activated to produce one or more beams 18a–c travelling through the object 26 on a first set of paths 20a–c. Next, the wheel 30 containing the filters 32, 34, is rotated to successively interpose each of the two filters 32, 34, between the X-ray source 12 and the object 26 to filter each of the beams 18 with each of the two filters 32, 34. This results in the production of two intensity-proportional signals by a detector 24 for each beam 18. It is to be appreciated that the two signals will be temporally spaced from each other, the spacing corresponding to the time the beam 18 strikes the wheel 30 between adjacent filters 32, 34.

Figure 5A:
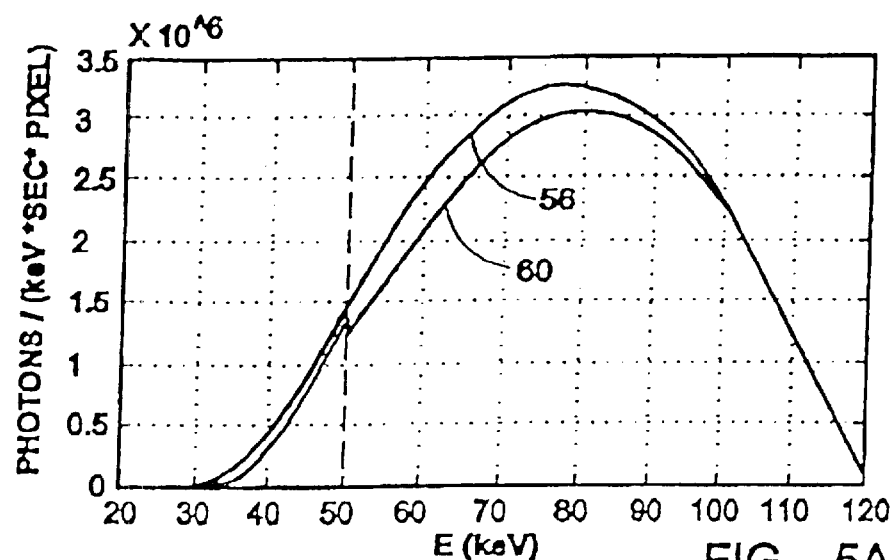
FIG. 5A is a graph showing an exemplary emission spectrum for a conventional X-ray source and a graph showing the spectrum that results after passing the same radiation through an object having a contrast agent with a $K_{EDGE}$ of approximately 50 keV.
Figure 5B:
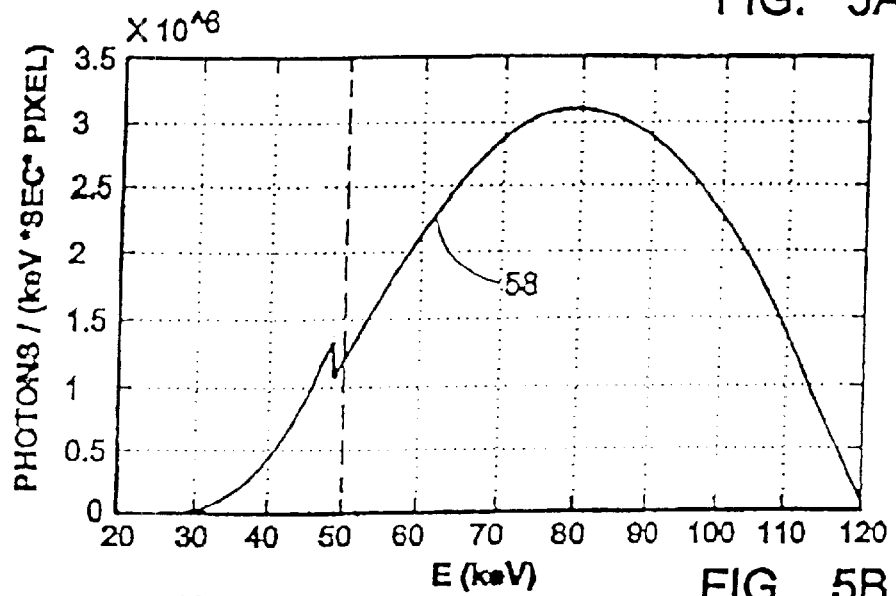
FIG. 5B is a graph showing the spectrum of a beam that results from passing an emission from a conventional X-ray source as shown in FIG. 5A through a filter having a chemical element with a $K_{EDGE}$ of approximately 49 keV.

Referring now to FIG. 5A, a typical emission spectrum for a conventional X-ray source 12 that has passed through a portion of the body having no contrast agent is shown by curve 56. When the spectrum represented by curve 56 reaches a detector 24, an electronic signal that is approximately proportional to the area under curve 56 (the intensity of the emission) is produced. Curve 60 in FIG. 5A represents the spectrum that results after radiation produced by a typical X-ray source 12 is passed through a portion of the body having exemplary contrast agent, Gd, in the absence of filters. Referring now to FIG. 5B, curve 58 represents the spectrum that results after radiation producing curve 56 in FIG. 5A is now passed through filter 34 and a portion of the body having no contrast agent. In this case, filter 34 has a filtering layer 48 having a chemical element with a $K_{EDGE}$ of approximately 49 keV. Accordingly, the electronic signal (hereinafter referred to as the filter 34 signal) produced by a detector 24 when filter 34 is interposed between the X-ray source 12 and the detector 24 will be approximately proportional to the area under curve 58.

Figure 5C:
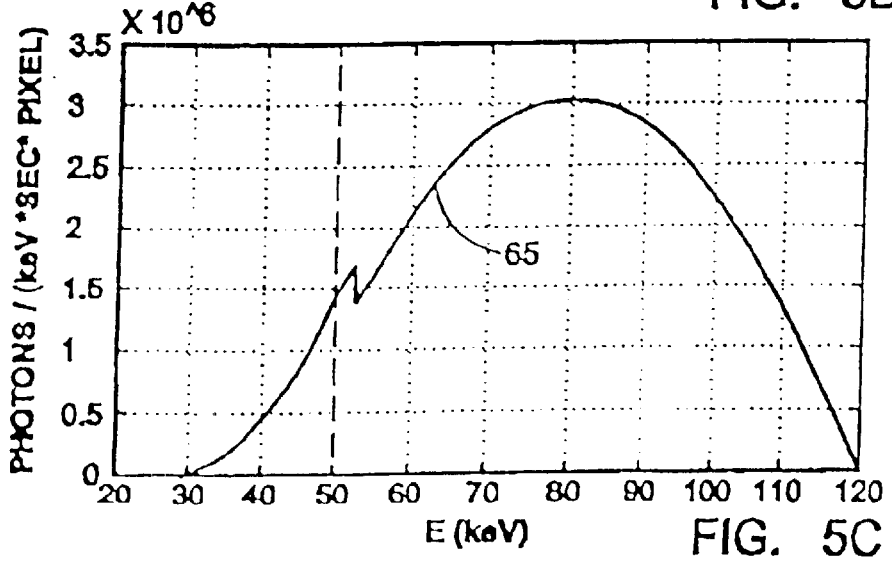
FIG. 5C is a graph showing the spectrum of a beam that results from passing an emission from a conventional X-ray source as shown in FIG. 5A through a filter having a chemical element with a $K_{EDGE}$ of approximately 52 keV.
Figure 6A:
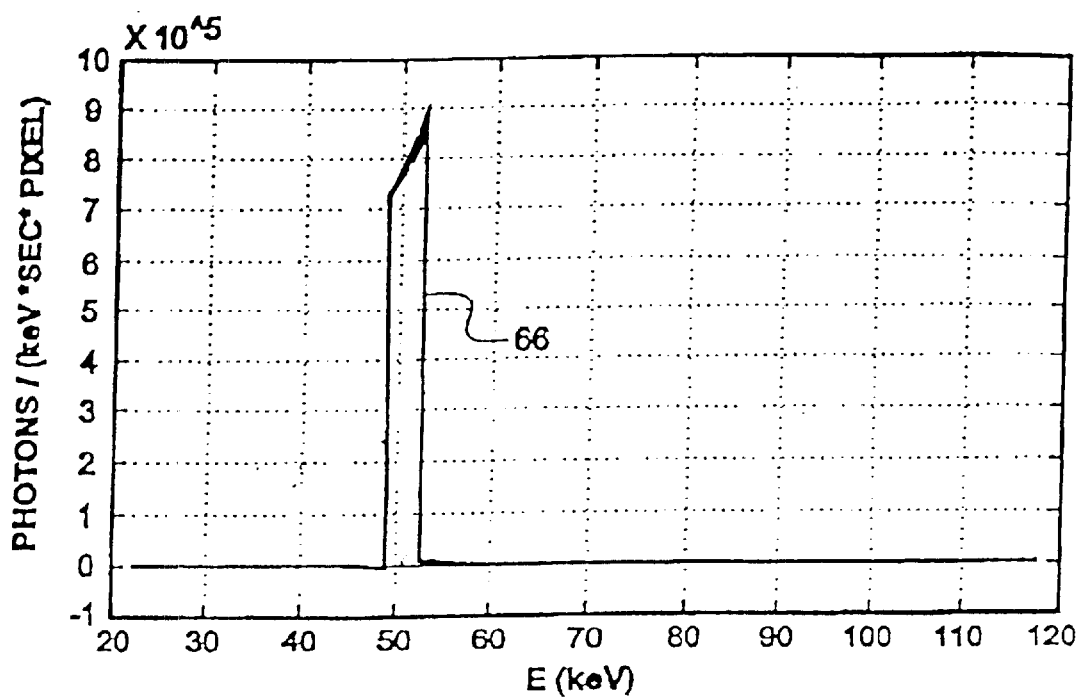
FIG. 6A is a graph showing a quasi-monochromatic radiation signal that is simulated by the filter pair and signal processing methods in accordance with the present invention for a portion of an object that does not contain a contrast agent.
Figure 6B:
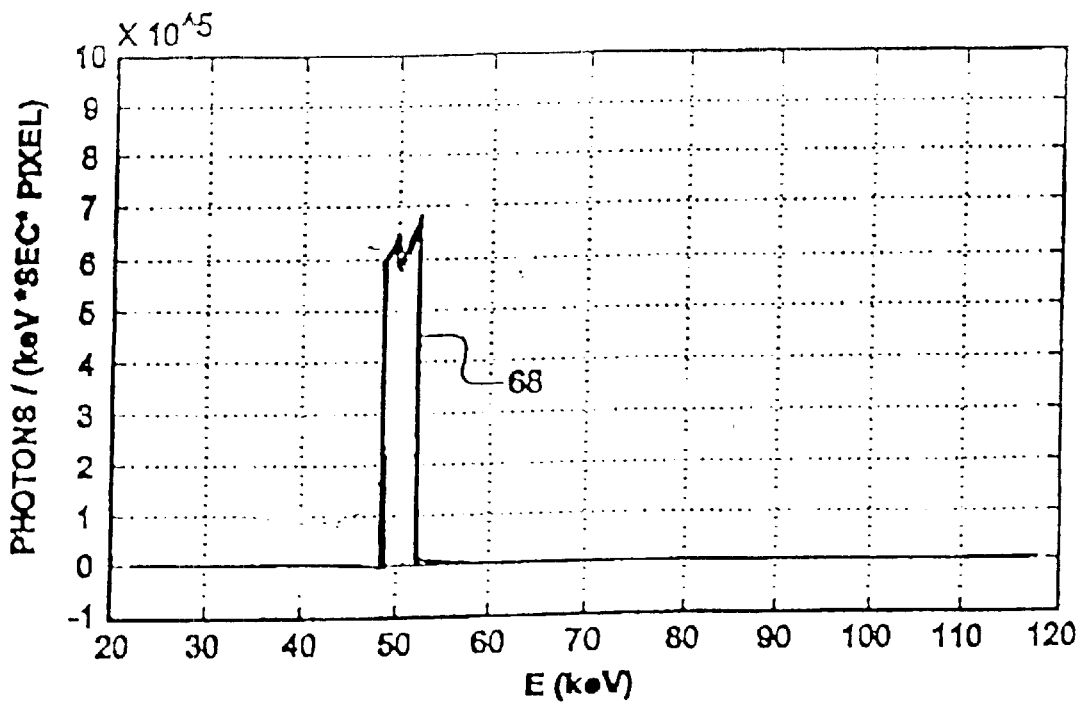
FIG. 6B is a graph showing a quasi-monochromatic radiation signal that is simulated by the filter pair and signal processing methods in accordance with the present invention for a portion of the object that contains a contrast agent.

Similarly, a curve representing the spectrum that results after radiation producing curve 65 in FIG. 5A is now passed through filter 32 and a portion of the body having no contrast agent is shown in FIG. 5C and designated curve 65. Accordingly, the electronic signal (hereinafter referred to as the filter 32 signal) produced by a detector 24 when filter 32 is interposed between the X-ray source 12 and the detector 24 will be approximately proportional to the area under curve 58. The processor subtracts the filter 34 signal produced by the detector 24 with the filter 34 interposed along the path 20 from the filter 32 signal produced by the detector 24 with the filter 32 interposed along the path 20 to produce an image signal for the path 20. It is to be appreciated that the image signal simulates an image signal that would be obtained if a quasi-monochromatic beam having an average energy approximately equal to $K_{EDGE\ CONTRAST\ AGENT}$ were to be passed through the object 26. More specifically, the image signal produced for paths 20 having no contrast agent simulates the exemplary quasi-monochromatic spectrum shown in FIG. 6A and designated 66. Similarly, the image signal produced for paths 20 having contrast agent simulates the exemplary quasi-monochromatic spectrum shown in FIG. 6B and designated 68. These image signals constitute the data processed for tomography or angiography. The image signal strongly varies with concentration and thickness of the contrast element due to the variation of absorption. This results in an enhanced contrast image between the region with the contrast agent and the region without.

Figure 7:
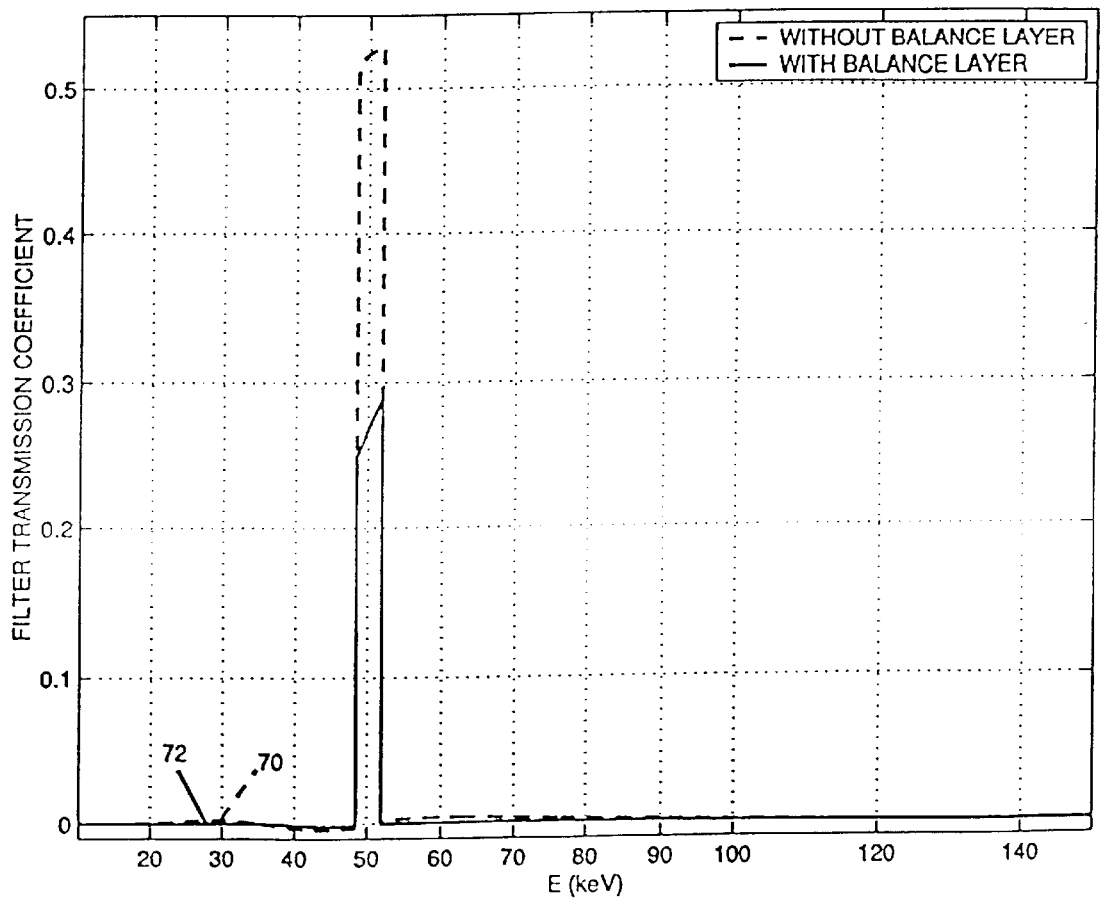
FIG. 7 is a graph showing the performance effect achieved when an additional balance layer is incorporated in a filter.

Referring now to FIG. 7, the effect of additional balance layers 50 in a filter pair is shown. Specifically, FIG. 7 compares the quasi-monochromatic signal that is simulated without additional balance layers 50 (curve 70) and the quasi-monochromatic signal that is simulated with additional balance layers 50 (curve 72). The curve 72 was generated for a filter pair having a filter 32 with a filtering layer 48 that includes 140.0 $\mu$m of $^{65}$Tb and an additional balance layer 50 of 200.0 $\mu$m of $^{65}$Tb and a filter 34 with a filtering layer 48 that includes 236.0 $\mu$m of $^{63}$Eu and an additional balance layer 50 of 200.0 $\mu$m of $^{65}$Tb. With cross reference to Table 1 and FIG. 7, these two filters 32, 34 can be used in a filter pair in conjunction with the contrast agent Gd to generate the image signal. As shown in FIG. 7, the use of additional balance layers 50 reduces the non-zero difference of the filter transmission outside the energy pass band. Of course, this effect is obtained by paying the price of reducing the radiation intensity within the pass band (by a factor of about two, in this case). In practice, the additional balance layer 50 is designed to provide a compromise between the enhancement of the quality of monochromatization (i.e. a thicker additional balance layer 50 providing better balance) and the intensity level within the energy pass band (i.e. a larger number of photons to provide a better Signal-To-Noise ratio).

Referring back to FIG. 2, once image signals are obtained for the first set of paths 20a–c, the X-ray source 12 and collimator 16 can be moved to a second position (shown by dashed lines) to cause the beams 18a–c emanating from the collimator 16 to travel along a new set of paths 20d–f. While the X-ray source 12 and collimator 16 are at the second position, the wheel 30 is again rotated to successively interpose each of the filters 32, 34 between the X-ray source 12 and the object 26 to again filter each of the beams 18a–c with each of the two filters 32, 34. Again, two intensity-proportional signals are produced by a detector 24 for each beam 18. For the present invention, these two signals can be manipulated by a processor (not shown) to produce image signals for each new path 20d–f. This process of moving the X-ray source 12 and producing two image signals for each new path 20 can be repeated as desired. Further, it is to be appreciated that the X-ray source 12 can be moved continuously around the object 26. When this technique is used, the wheel 30 containing filter 32 and filter 34 can be rotated continuously as the X-ray source 12 moves. By rotating the wheel 30 very rapidly, each beam 18 can be filtered by each filter 32, 34 before significant movement of the beam 18 occurs. Thus, in effect, each beam 18 remains on a single path 20 while the successive filtration takes place. It is to be appreciated that the image signals described above may also be obtained by first acquiring electrical signals for all paths 18 with the filter 32 interposed along the paths 18, followed by the acquisition of electrical signals for all paths 18 with filter 34 interposed along the paths 18. Once an image signal is produced for all paths 20 of interest, conventional tomography techniques can be used to combine all the image signals (one image signal for each path 20) into a composite image that shows the internal features of the object 26.

Figure 8A:
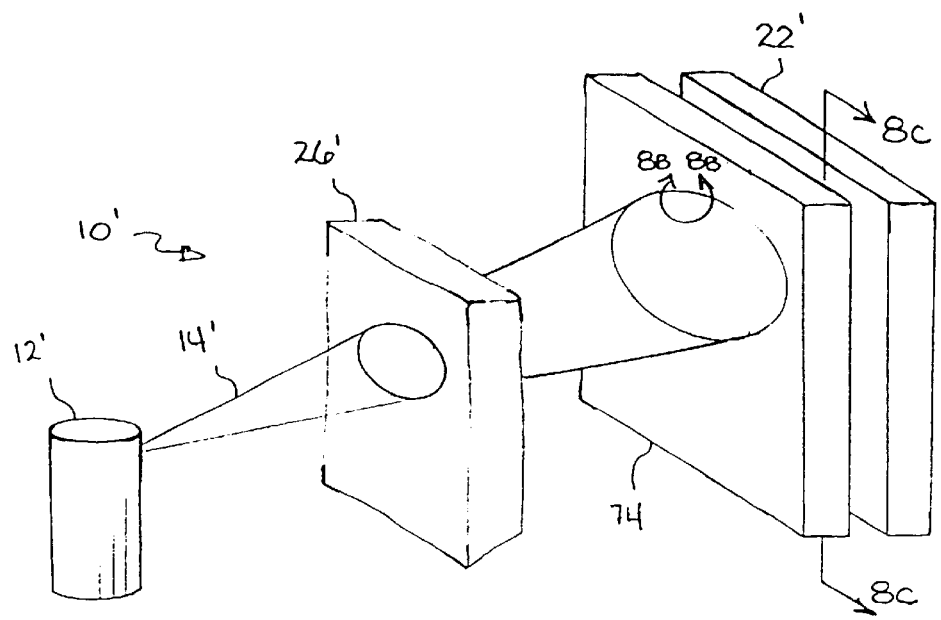
FIG. 8A is a perspective view showing an alternate embodiment for the present invention in which a stationary filter set is constructed as a two dimensional array.
Figure 8C:
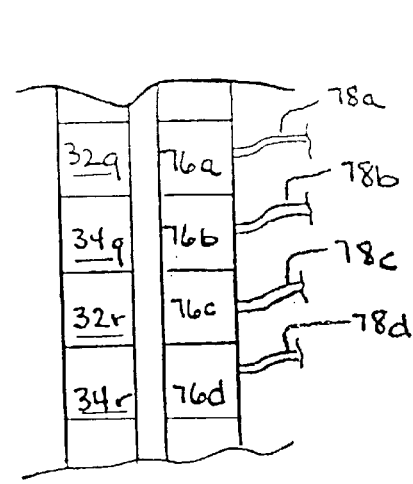
FIG. 8C is an enlarged sectional view of a portion of the filter set and detector array as seen along line 8C—8C in FIG. 8A.
Figure 8B:
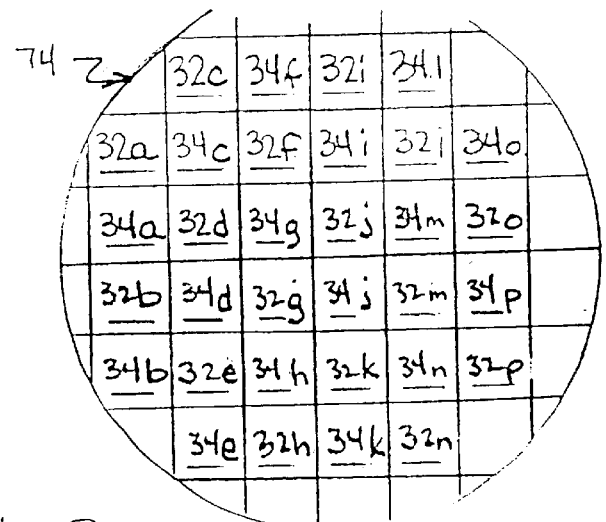
FIG. 8B is an enlarged, elevation view of a portion of a filter set as seen along line 8B—8B in FIG. 8A showing the alternating pattern of filters in the two dimensional array.

Referring now to FIGS. 8A–8C, another embodiment of an imaging system in accordance with the present invention is shown and generally designated 10'. As shown in FIG. 8A, the system 10' includes an X-ray source 12' configured to produce a spectrum of X-ray radiation 14'. As further shown, a detector array 22' is shown positioned to receive the radiation 14' from the source 12'. For the present invention, an object 26' is interposed between the X-ray source 12' and the detector array 22' to thereby allow the radiation 14' to be modified by passing through the object 26' before reaching the detector array 22'. For the present embodiment, the object 26' can be a human body, suitcase, machine component or any other object that requires internal imaging. As further shown, a filter set 74 is provided to filter the radiation 14' before the radiation 14' reaches the detector array 22'. Preferably, in this embodiment, the filter set 74 and detector array 22' are stationary during the imaging procedure.

With cross reference now to FIGS. 8A, 8B and 8C, it can be seen the filter set 74 includes a plurality of filters 32 and a plurality of filters 34. It is to be appreciated that the filters 32a–p and 34a–p (see FIG. 8B) as well as the filters 32q–r and 34q–r (see FIG. 8C) are only exemplary. As best seen in FIG. 8B, the filters 32, 34 are preferably arranged in a planar, two dimensional array. For an object 26' having a contrast agent containing a chemical element having a $K_{EDGE\ CONTRAST\ AGENT}$, each filter 32 contains a chemical element having a $K_{EDGE}$ that is greater than $K_{EDGE,\ CONTRAST\ AGENT}$, and each filter 34 contains a chemical element having a $K_{EDGE}$ that is less than $K_{EDGE\ CONTRAST\ AGENT}$. It is to be further appreciated that the specific chemical elements and thickness' shown in Table 1 can be used to prepare the filters 32, 34 in the filter set 74.

As best seen in FIG. 8B, within the planar, two dimensional array, the filters 32, 34 are preferably arranged in an alternating, checker board pattern. With this pattern, a plurality of filter pairs is established, with each pair containing one filter 32 and an adjacent filter 34. For example, filter 32a and 34a constitute a filter pair for the present invention. Similarly, filter 32b and 34b constitute a filter pair for the present invention and so on.

As best seen with cross reference to FIGS. 8A and 8C, the detector array 22' includes a planar array of detectors 76, of which detectors 76a–d are exemplary, with one detector 76 for each filter 32, 34. In accordance with the present invention, the detector array 22' is preferably an amorphous silicon array of digital detectors 76, with each detector 76 producing an electrical signal that is proportional to the intensity of the radiation received. Furthermore, a pair of detectors 76, such as detector 76a and detector 76b, is provided for each filter pair (32, 34). As shown, the detector pair 76a, 76b is positioned to receive filtered radiation from the filter pair (32q, 34q). For the present invention, the output of each detector 76 is electrically wired (via wires 78, of which wires 78a–d are exemplary) to a computer (not shown) to allow the signals generated by the detectors 76 to be processed. It is to be appreciated that for each filter pair (32, 34), a corresponding pair of detectors 76 produces two different electrical signals (i.e. one electrical signal for filtration with filter 32 and one electrical signal for filtration with filter 34).

For the present invention, a computer processor (not shown) can be configured to manipulate the two electrical signals created for each filter pair to produce an image signal for the filter pair (32, 34). More specifically, the processor subtracts the electrical signal corresponding to filtration with filter 34 from the electrical signal corresponding to filtration with filter 32 to produce an image signal for the filter pair (32, 34). It is to be appreciated that each filter pair (32, 34) can be used to produce an image signal that represents a single pixel in the final image. Once an image signal is established for each filter pair (32, 34), the processor can be used to combine all the image signals (one image signal for each filter pair (32, 34) into a composite image that shows the internal features of the object 26'.

In another embodiment of the present invention, the detector array 22' and filter set 74 as shown in FIG. 8a are formed as linear arrays. It is to be appreciated that a single filter pair 32, 34 can be used in this embodiment. Preferably, for this embodiment, the X-ray source 12', linear detector array 22' and filter set 74 are mounted on a track (such as the track 28 shown in FIG. 2) for movement relative to the object 26'. During imaging, the X-ray source 12' is moved along the track 28 to successive positions, and an image signal is generated (as described above) from the filter pair (32, 34) for each position of the X-ray source 12'. Once an image signal is produced for each desired position of the X-ray source 12', conventional tomography techniques can be used to combine all the image signals into a composite image that shows the internal features of the object 26'.

While the particular imaging systems and methods as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A system for creating an image of an object, said object containing a first chemical element having a $K_{EDGE,\ FIRST\ CHEMICAL\ ELEMENT}$, said system comprising:

an X-ray source configured to emit an X-ray beam along a first path through said object;

means for moving said beam onto successive paths through said object;

a first filter and a second filter, said first filter comprising a chemical element having a $K_{EDGE}$ greater than $K_{EDGE,\ FIRST\ CHEMICAL\ ELEMENT}$ and said second filter comprising a chemical element having a $K_{EDGE}$ less than $K_{EDGE,\ FIRST\ CHEMICAL\ ELEMENT}$;

a means for successively positioning said filters on each said path to filter said beam and produce a first filtered radiation signal and a second filtered radiation signal for each said path through said object;

a detector for receiving said first and second radiation signals after said signals have passed through said object and producing a first and second electrical signal for each said path, said electrical signals produced by said detector being proportional to the intensity of the radiation received by said detector; and a processor connected to said detector to generate an image signal for each said path through said object wherein said image signal is proportional to a difference between said first and second electrical signals, said processor configured to produce an image of said object from said image signals.

2. A system as recited in claim 1 wherein said means for successively positioning said filters comprises:

a wheel defining an axis and formed with a pair of holes, each said hole for accommodating a said filter; and means for selectively rotating said wheel about said axis.

3. A system as recited in claim 1 wherein said means for selectively rotating said wheel about said axis is a motor and said motor and wheel are mounted on said X-ray source for movement therewith.

4. A system for creating an image of an object that contains a contrast agent, said system comprising:

a means for directing a spectrum of electromagnetic radiation onto a plurality of paths, each said path extending through said object;

a first filter and a second filter, each said filter comprising at least one chemical element having a $K_{EDGE}$ within said spectrum of said electromagnetic radiation;

a means for successively interposing each said filter on each said path to create a first filtered radiation signal and a second filtered radiation signal for each said path;

a means for receiving said filtered radiation signals and producing an electrical signal for each said filtered radiation signal received, each said electrical signal being proportional to the intensity of radiation received; and a processor for operation on said electrical signals to produce an image of said object.

5. A system as recited in claim 4 wherein said interposing means is positioned to successively interpose each said filter on each said path to contact said radiation before said radiation passes through said object.

6. A system as recited in claim 4 wherein said means for successively interposing each said filter on each said path comprises:

a wheel defining an axis and formed with a plurality of holes, each said hole for accommodating a said filter; and means for selectively rotating said wheel about said axis.

7. A system as recited in claim 4 wherein said contrast agent comprises a chemical element having a $K_{EDGE,\ CONTRAST\ AGENT}$ and said first filter comprises a chemical element having a $K_{EDGE}$ greater than $K_{EDGE,\ CONTRAST\ AGENT}$, and said second filter comprises a chemical element having a $K_{EDGE}$ less than $K_{EDGE,\ CONTRAST\ AGENT}$.

8. A system as recited in claim 7 wherein said contrast agent comprises the chemical element Iodine, said first filter comprises a layer of the chemical element Cs at an approximate thickness of 290 $\mu$m and said second filter comprises a layer of the chemical element Te at an approximate thickness of 102 $\mu$m.

9. A system as recited in claim 7 wherein said contrast agent comprises the chemical element Xe, said first filter comprises a layer of the chemical element Ba at an approximate thickness of 180 $\mu$m and said second filter comprises a layer of the chemical element Te at an approximate thickness of 123 $\mu$m.

10. A system as recited in claim 7 wherein said contrast agent comprises the chemical element Cs, said first filter comprises a layer of the chemical element Ba at an approximate thickness of 180 $\mu$m and said second filter comprises a layer of the chemical element I at an approximate thickness of 148 $\mu$m.

11. A system as recited in claim 7 wherein said contrast agent comprises the chemical element Ba, said first filter comprises a layer of the chemical element La at an approximate thickness of 105 $\mu$m and said second filter comprises a layer of the chemical element Cs at an approximate thickness of 380 µm.

12. A system as recited in claim 7 wherein said contrast agent comprises the chemical element Sm, said first filter comprises a layer of the chemical element Eu at an approximate thickness of 136 µm and said second filter comprises a layer of the chemical element Nd at an approximate thickness of 117 µm.

13. A system as recited in claim 7 wherein said contrast agent comprises the chemical element Eu, said first filter comprises a layer of the chemical element Gd at an approximate thickness of 120 µm and said second filter comprises a layer of the chemical element Sm at an approximate thickness of 138 µm.

14. A system as recited in claim 7 wherein said contrast agent comprises the chemical element Gd, said first filter comprises a layer of the chemical element Tb at an approximate thickness of 140 µm and said second filter comprises a layer of the chemical element Eu at an approximate thickness of 236 µm.

15. A system as recited in claim 7 wherein said contrast agent comprises the chemical element Tb, said first filter comprises a layer of the chemical element Dy at an approximate thickness of 130 µm and said second filter comprises a layer of the chemical element Gd at an approximate thickness of 151 µm.

16. A system as recited in claim 7 wherein said contrast agent comprises the chemical element Dy, said first filter comprises a layer of the chemical element Ho at an approximate thickness of 130 µm and said second filter comprises a layer of the chemical element Tb at an approximate thickness of 149 µm.

17. A system as recited in claim 7 wherein said contrast agent comprises the chemical element Ho, said first filter comprises a layer of the chemical element Er at an approximate thickness of 130 µm and said second filter comprises a layer of the chemical element Dy at an approximate thickness of 149 µm.

18. A system as recited in claim 7 wherein said contrast agent comprises the chemical element Er, said first filter comprises a layer of the chemical element Tm at an approximate thickness of 135 µm and said second filter comprises a layer of the chemical element Ho at an approximate thickness of 156 µm.

19. A system as recited in claim 7 wherein said contrast agent comprises the chemical element Lu, said first filter comprises a layer of the chemical element Hf at an approximate thickness of 110 µm and said second filter comprises a layer of the chemical element Yb at an approximate thickness of 235 µm.

20. A system as recited in claim 7 wherein said contrast agent comprises the chemical element Hf, said first filter comprises a layer of the chemical element Ta at an approximate thickness of 97 µm and said second filter comprises a layer of the chemical element Lu at an approximate thickness of 175 µm.

21. A system as recited in claim 7 wherein said contrast agent comprises the chemical element Ta, said first filter comprises a layer of the chemical element W at an approximate thickness of 84 µm and said second filter comprises a layer of the chemical element Hf at an approximate thickness of 131 µm.

22. A system as recited in claim 7 wherein said contrast agent comprises the chemical element W, said first filter comprises a layer of the chemical element Re at an approximate thickness of 80 µm and said second filter comprises a layer of the chemical element Ta at an approximate thickness of 108 µm.

23. A system as recited in claim 7 wherein said contrast agent comprises the chemical element Re, said first filter comprises a layer of the chemical element Os at an approximate thickness of 80 µm and said second filter comprises a layer of the chemical element W at an approximate thickness of 100 µm.

24. A system as recited in claim 7 wherein said contrast agent comprises the chemical element Os, said first filter comprises a layer of the chemical element Ir at an approximate thickness of 80 µm and said second filter comprises a layer of the chemical element Re at an approximate thickness of 90 µm.

25. A system as recited in claim 7 wherein said contrast agent comprises the chemical element Ir, said first filter comprises a layer of the chemical element Pt at an approximate thickness of 90 µm and said second filter comprises a layer of the chemical element Os at an approximate thickness of 92 µm.

26. A system as recited in claim 7 wherein said contrast agent comprises the chemical element Bi, said first filter comprises a layer of the chemical element Th at an approximate thickness of 170 µm and said second filter comprises a layer of the chemical element Pb at an approximate thickness of 230 µm.

27. A method for creating an image comprising the steps of:

provided an object;

directing a spectrum of electromagnetic radiation onto a plurality of paths, each said path extending through said object;

providing a first filter and a second filter, each said filter comprising at least one chemical element having a $K_{EDGE}$ within said spectrum of said electromagnetic radiation;

successively interposing each said filter on each said path to create a first filtered radiation signal and a second filtered radiation signal for each said path;

receiving said filtered radiation signals for each said path and producing an electrical signal for each said filtered radiation signal received, each said electrical signal being proportional to the intensity of radiation received; and processing said electrical signals to produce an image of said object.

28. A method as recited in claim 27 further comprising the step of administering a contrast agent into said object.

29. A method as recited in claim 27 wherein said object is a human body.

30. A system for creating an image of an object, said object containing a first chemical element having a $K_{EDGE, \text{ FIRST CHEMICAL ELEMENT}}$, said system comprising:

a means for directing X-ray radiation through said object;

a plurality of filter pairs with each said filter pair having a first filter comprising a chemical element having a $K_{EDGE}$ greater than $K_{EDGE, \text{ FIRST CHEMICAL ELEMENT}}$ and a said second filter comprising a chemical element having a $K_{EDGE}$ less than $K_{EDGE, \text{ FIRST CHEMICAL ELEMENT}}$, each said filter pair positioned to filter said radiation and produce a pair of filtered radiation signals;

a plurality of detector pairs, each said detector pair for receiving one said pair of filtered radiation signals from one said filter pair and producing a pair of electrical signals in response, with each said electrical signal being proportional to the intensity of radiation received by a said detector; and a processor connected to said detector pairs to generate an image signal for each said detector pair, wherein said image signal is proportional to a difference between electrical signals in each said pair of electrical signals to produce an image of said object from said image signals.

31. A system as recited in claim 30 wherein said first and second filters of each said filter pair are positioned adjacent to each other.

32. A system as recited in claim 30 wherein said plurality of filter pairs is arranged as a planar array.

33. A system as recited in claim 32 wherein said plurality of filter pairs is arranged to create a two-dimensional, alternating pattern of first filters and second filters.

34. A system as recited in claim 30 wherein said object is a human body.

35. A system as recited in claim 30 further wherein said directing means is an X-ray source and further comprising a means for moving said X-ray source, said plurality of filter pairs and said plurality of detector pairs relative to said object during imaging of said object.

* * * * *